US007658942B2

(12) United States Patent
Deckner et al.

(10) Patent No.: US 7,658,942 B2
(45) Date of Patent: Feb. 9, 2010

(54) COSMETIC DEVICES

(75) Inventors: George Endel Deckner, Cincinnati, OH (US); Delyth Myfanwy Jenkins, Egham (GB); Kenneth Eugene Kyte, Lebanon, OH (US); Michael Jude LeBlanc, Cincinnati, OH (US); Jennifer Elizabeth Phillips, Atlanta, GA (US)

(73) Assignee: The Procter & Gamble Company, Cincinnati, OH (US)

( * ) Notice: Subject to any disclaimer, the term of this patent is extended or adjusted under 35 U.S.C. 154(b) by 227 days.

(21) Appl. No.: 10/268,556

(22) Filed: Oct. 10, 2002

(65) Prior Publication Data

US 2003/0113356 A1 Jun. 19, 2003

Related U.S. Application Data

(63) Continuation of application No. PCT/US00/09694, filed on Apr. 12, 2000.

(51) Int. Cl.
*A61K 9/70* (2006.01)
*A61K 8/02* (2006.01)

(52) U.S. Cl. ............... 424/449; 424/400; 424/402; 424/443; 424/448; 424/485

(58) Field of Classification Search ............ 424/402, 424/449, 400, 424, 443, 448, 485
See application file for complete search history.

(56) References Cited

U.S. PATENT DOCUMENTS

| 4,743,249 | A | * | 5/1988 | Loveland | ............... 424/447 |
| 4,943,435 | A | * | 7/1990 | Baker et al. | ............... 424/448 |
| 5,626,866 | A | * | 5/1997 | Ebert et al. | ............... 424/447 |
| 5,723,138 | A |   | 3/1998 | Bae et al. | |
| 5,785,978 | A |   | 7/1998 | Porter et al. | |
| 5,962,482 | A | * | 10/1999 | Bissett | ............... 514/356 |
| 5,965,154 | A | * | 10/1999 | Haralambopoulos | ........ 424/449 |
| 5,985,300 | A | * | 11/1999 | Crotty et al. | ............... 424/402 |
| 6,180,133 | B1 | * | 1/2001 | Quan et al. | ............... 424/448 |
| 6,322,799 | B1 | * | 11/2001 | Ilardi et al. | ............... 424/401 |

FOREIGN PATENT DOCUMENTS

| EP | 0161681 A2 | 11/1985 |
| EP | 0 392845 A2 | 10/1990 |
| GB | 2265086 A | 9/1993 |
| JP | UM58-176931 | 11/1983 |
| JP | UMH3-39027 | 4/1991 |
| JP | 9-122221 A | 5/1997 |
| JP | 9-316413 A | 12/1997 |
| JP | 10-17448 A | 1/1998 |
| JP | 11-130625 | 6/1999 |
| NZ | 329525 | 5/1999 |
| WO | WO 97/17944 | 5/1997 |
| WO | WO 98/42303 | 10/1998 |
| WO | WO 01/01950 | 1/2001 |

OTHER PUBLICATIONS

Ansel, H. et al. Pharm. Dosage Forms and Drug Delivery Systems, 1990, Lea & Febiger, 5th Ed., pp. 310-320.*

* cited by examiner

*Primary Examiner*—Gina C Yu
(74) *Attorney, Agent, or Firm*—Eric T. Addington; John M. Howell; S. Robert Chuey

(57) ABSTRACT

The present invention relates to pre-formed devices for delivering benefit agents to the skin, hair or nails. The devices are patches or masks for cosmetic or therapeutic use and comprise a unilamellar, solid gel sheet having at least one surface at least partially coated with a discrete coating composition comprising at least one benefit agent for the skin, hair or nails. The invention also encompasses methods of producing and using such devices. The coating composition allows more efficient delivery of benefit agents to the skin than previously known devices and/or affords greater formulation flexibility.

16 Claims, 1 Drawing Sheet

COSMETIC DEVICES

CROSS REFERENCE TO RELATED APPLICATION(S)

This application claims priority to International Application No. PCT/US00/09694, filed Apr. 12, 2000.

TECHNICAL FIELD

The present invention relates to pre-formed devices in the form of a gel sheet for delivering benefit agents to the skin, hair or nails. More particularly the invention relates to gel sheets having a coating composition on at least one surface. The coating composition comprises at least one skin benefit agent and allows more efficient delivery of benefit agents to the skin than previously known, uncoated sheets and/or affords greater formulation flexibility.

BACKGROUND OF THE INVENTION

The benefits of using a patch or mask device comprising a polymeric gel forming agent instead of creams and lotions and the like, to cosmetically treat the skin, hair or nails, or to promote the healing of burns or wounds have been recognised in the art. A variety of cosmetic patches or devices are commercially marketed or described as being useful for the delivery of skin care actives such as vitamins, anti-acne actives, moisturisers and the like. Patches have also been described in the literature and marketed in the medical field as a useful means for the transdermal administration of drugs. However, many patches or similar devices suffer drawbacks in their physical product forms resulting in undesirable in-use characteristics as perceived by the consumer or wearer. For example, some patches or devices may be too wet or sticky, as the gel forming agents comprising the patch or device do not form a solid gel structure and as a result, the patches or devices are difficult to handle and apply to the skin. Others are strongly adhesive, tight and uncomfortable to wear and remove, and many patches do not provide an effective release and penetration of benefit agents. Further, some patches or devices are too dry or inflexible and therefore do not conform well to the contours of the surface to which they are applied.

WO 97/17944 discloses structured cosmetic gel formulations which are optionally enriched with water-soluble or water-dispersible active ingredients. The optional ingredients are incorporated during gel formation.

Several applications disclose active agents, such as vitamins, incorporated into pressure-sensitive adhesive devices. GB-A-2 265 086, for example, describes skin whitening patches in which skin whitening agents and other ingredients, such as permeation enhancers and glycerin, are formulated into an adhesive layer attached to an impermeable backing. U.S. Pat. No. 5,785,978 teaches the incorporation of vitamins, especially vitamin C, in powder form into an adhesive layer which also has an impermeable backing. U.S. Pat. No. 5,965,154 also relates to the incorporation of active ingredients such as powdered vitamin C into an adhesive layer. WO 98/42303 is yet a further publication dealing with the incorporation of active ingredients such as powdered vitamin C into a product which has a substrate and a layer comprising an adhesive polymer. In this application the function of the adhesive layer is to strip away keratotic plugs. Its substrate layer is preferably non-occlusive. U.S. Pat. No. 5,723,138 teaches products in which cosmetic ingredients, for preventing removing or alleviating wrinkles, are incorporated into adhesives and applied to a tape.

EP-A-161 681 discloses polysaccharide gel plates for use as poultices. The plates may comprise medical components such as skin stimulants, antiphlogistics, analgesics and antibiotics. The medical component can be incorporated into the plate as the plate is formed or subsequently coated or impregnated with a solution or dispersion of the component. In the case of subsequent addition of the medical component it is taught that the intermediate gel plate product is dried to give it a high absorbency for the medical component.

NZ 329525 describes a method of treating the skin comprising applying a cosmetic preparation to the skin and then applying a dressing over the top. JP 11-130625 describes an acrylic gel based sheet pack for treatment of facial wrinkles. Optionally, a separate lotion can be applied to the face before the pack is applied. Likewise, commercial products are sold in Japan, such as Sofina Seraty Wrinkle Device Eye Patch from Kao Corporation, which recommend pre-treatment of the face with a gel or lotion before the sheet is applied to the face. Such products may be sold as kits and require separate application of a gel/lotion and a sheet.

Co-pending PCT application no. PCT/US99/15202 discloses gel patches which comprise cosmetic agents dispersed within them but which exhibit a moderate amount of syneresis so that an exudate will be released onto the surface.

It has now been found that the efficacy of a gel sheet in delivering benefit agents to the skin, hair or nails can be improved by coating a pre-formed gel sheet with a discrete, separate coating composition comprising at least one skin benefit agent. Furthermore, this structure for a gel device allows greater formulation flexibility e.g. by allowing the incorporation of benefit agents, such as powders, which would not otherwise migrate out of a gel matrix, or by allowing drier gels which are easier to handle or more pleasant to the touch where they are non-coated.

The gel devices herein are patches or masks for cosmetic or therapeutic application.

SUMMARY OF THE INVENTION

The present invention relates to a pre-formed device for delivering benefit agents to the skin, hair or nails, the device comprising a solid gel sheet having opposed first and second surfaces, wherein the gel sheet comprises one or more gelling agents and at least 10% dermatologically acceptable hydrophilic solvent, characterised in that the first surface is at least partially coated with a discrete coating composition comprising at least one benefit agent for the skin, hair or nails. Methods of manufacture and use of the coated devices are also provided.

The use of a coating composition allows more efficient delivery of benefit agents to the skin than previously known devices and affords greater formulation flexibility. The pre-formed, coated devices of the present invention provide excellent hydration and moisturisation benefits upon topical application as well as chronic benefits by improved delivery of topically effective actives. Further, the pre-formed devices of the present invention have excellent mechanical and optical properties, having a high strength structure which is flexible, elastic and optically clear, thus providing desirable in-use characteristics such as unobtrusiveness and conformability. The coating composition allows more efficient delivery of benefit agents to the skin than previously known devices and/or affords greater formulation flexibility.

DETAILED DESCRIPTION OF THE INVENTION

Figure 1:
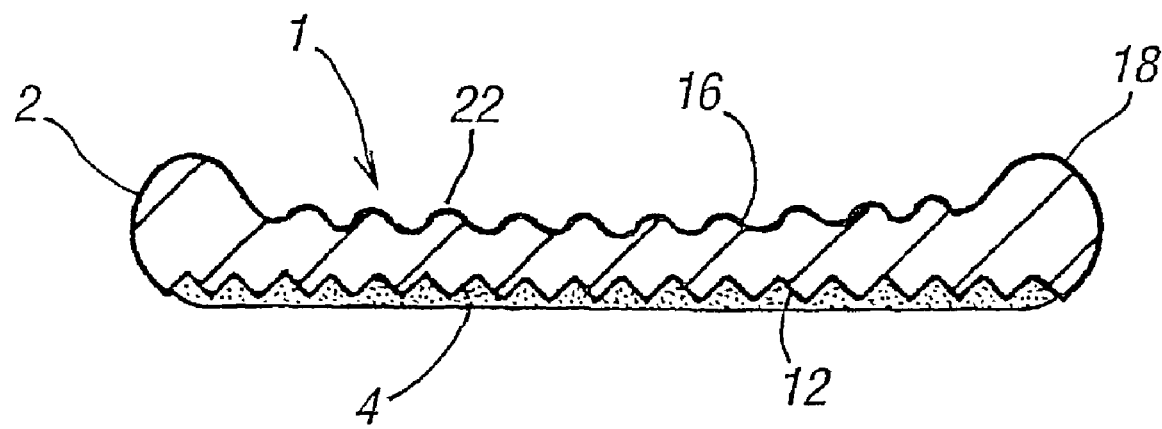
FIG. 1 is a sectional view of a device according to the invention, the gel sheet of the device is textured on first and second surfaces and a coating has been applied to the first surface.

The pre-formed devices of the present invention comprise a solid gel sheet and a discrete coating composition. All levels and ratios of gel sheet components are by weight of the gel sheet, and all levels and ratios of coating composition components are by weight of the coating composition, unless otherwise indicated. All measurements herein are made at 25° C., unless otherwise specified. The invention particularly relates to pre-formed devices which are manufactured on an industrial scale and packaged in protective wrappers, for shipment and retail sale. The devices are used for delivering benefit agents to the skin, hair or nails, preferably the skin or nails, most preferably the skin, in particular facial skin.

The term "pre-formed" as used herein, means that the device is manufactured into a form having a predetermined thickness, shape and size, wherein the device may be removed from any associated packaging and placed or draped onto the target surface by the fingers without further preparative steps by the user.

The term "gel sheet", as used herein, means a patch or mask, for cosmetic or medical application, which is a continuous, uni-, bi-, or multi-lamellar sheet, the shape of which is pre-determined according to the specific area of skin, hair or nails to be treated, masks being designed to cover the facial area and having apertures for the eyes, nose or mouth. Preferred gel sheets are unilamellar, by which is meant that they comprise a single layer.

"Solid" as used in reference to gel sheets herein, means that the sheet substantially retains its shape at 25° C. when lying on a flat surface. The sheet may nevertheless flex or be deformed when applied to an uneven surface or if impressed.

The term "hydrophilic" as used in reference to solvents herein, means that the solvent is miscible with water, at least in a solvent to water ratio of 1 to 10, preferably 1 to 5.

The term "water-soluble" as used herein, means the ability of a gellable polymeric gel forming agent to dissolve in an aqueous solution either at room temperature or upon heating thereby forming a continuous phase.

The term "syneresis" as used herein, means the process whereby a gel contracts on standing with the exudation of liquid. Without being limited by theory, it is believed that gel compositions herein form 3-dimensional matrices which bind or encapsulate other ingredients of the composition. Syneresis is believed to involve a spontaneous separation of an initial homogeneous system into a coherent gel phase and a liquid. The exuded liquid is a solution whose composition depends upon that of the original gel.

The term "polysaccharide" herein means a naturally occurring or synthetically produced, linear, branched or cross-linked polymer of monosaccharide units, which swells when dispersed in water at low concentrations and thickens the aqueous phase.

The term "non-planar topography" refers to at least two adjacent delineated areas of a surface of the device, or of an auxiliary surface for applying a non-planar topography to the device, lying in different planes such that the surface is textured. The texture can be rough, undulating or stepped and can be regular or irregular.

The term "periodicity" as used herein, means a pattern of repeating units and is a measure of the distance between the start point and end point of a repeat unit of pattern.

Gel Sheets

The pre-formed devices of the present invention comprise a solid gel sheet. The sheet provides the primary structure and shape to the device, allowing it to be handled and to suit treatment of a specific target area of the skin, hair or nails. It can also act as a reservoir or as a delivery vehicle for benefit agents and, by virtue of evaporation of a solvent from the sheet, provide a cooling action to the device during use.

The gel sheets have a size and shape adapted to conform to a desired target area which could be the nails or cuticles, the hair or scalp, a human face or part thereof, legs, hands, arms, feet, or human torso. They are generally flat in appearance, having opposed first and second surfaces. Devices according to the present invention are generally of a size such that each surface has an area of from about 0.25 cm$^2$ to about 1,000 cm$^2$, preferably from about 1 cm$^2$ to about 100 cm$^2$. Surface area refers to that of a flat plane having the same boundary as the surface i.e. ignoring any surface texturing present. Generally, at least one surface dimension of the device, preferably both, is greater than the depth of the device, with preferred ratios of surface dimension(s) to depth of the device being in the range of from about 2:1 to about 100:1, more preferably from about 5:1 to about 50:1. The term "surface dimension" as used herein, means a dimension in the x- or y-axes, depth being measured along the z-axis.

The exact size and shape will depend upon the intended use and product characteristics. The devices herein can be, for example, square, circular, semicircular, rectangular, oval, rings, crescents, teardrops or other more complex shapes which may be composites of these. Devices shaped to fit the face have a surface area ranging from about 0.25 cm$^2$ to about 500 cm$^2$, preferably from about 1 cm$^2$ to about 400 cm$^2$. The devices generally have an average thickness of from about 0.5 mm to about 20 mm, preferably from about 0.7 mm to about 5 mm. Preferred devices have a thickened rim which is from about 0.1 to about 1.5 mm, preferably from about 0.2 to about 1 mm thicker than the central portion of the patch. It has been found that the thickened rim considerably increases patch strength towards handling without significantly reducing its flexibility.

Either or both of the first and second surfaces of the gel sheet can have a non-planar topography. The non-planar topography can be generalised across the surface of the patch, such as a surface texture, or can be a localised discontinuity such as a thickened peripheral rim. Preferably at least the first surface is textured, having a texture defined by $R_a$ of greater than about 10 μm. The texturing can have a pattern which is regular or irregular. The preferred pattern is sinusoidal, saw tooth or conical with a periodicity of from about 0.1 mm to about 10 mm, preferably from about 0.5 mm to about 5 mm. The texturing of the first surface is useful for improving the adhesion of the coating composition to the gel sheet. Texturing of the second surface, which in use will be distal to the skin, nails or hair, is useful for reducing surface shine, making the device less obtrusive whilst being worn. A thickened rim can provide some additional integrity to the device, enabling it to be handled more easily without tearing. Preferably, a non-planar topography, being either a textured surface or at least two delineated regions simultaneously not having the same mean thickness or both, is applied to both first and second surfaces of the gel sheet.

The gel sheets comprise as essential components, one or more gelling agents and at least 10% dermatologically acceptable hydrophilic solvent. They can also optionally comprise a variety of other ingredients, in particular benefit agents and auxiliary additives which are described in more detail below following the general description of the coating composition. The gelling agents and hydrophilic solvent will now be described in more detail.

Gelling Agents

In general, the gel sheets of the present invention comprise less than 70%, preferably less than 50%, more preferably less than 30% and especially less than 10% by total weight of a gelling agent. Many types of gelling agents, or gellants, are known in the art, including polymeric gellants and particulate based gellants such as various types of clays or other silicate based materials. Highly preferred herein are polymeric gelling agents from the point of view of the structure that they provide to the gels.

Polymeric gellants for use herein may be naturally or synthetically derived and can be self-gelling or may only form gels in combination with other substances. They may be physically or chemically cross linked. Some gelling agents form gels in combination with substances such as sugar, alcohol, or mono- or multi-valent salts. Mono- or multi-valent salts may additionally act as gel strengthening agents imparting added strength to the gel sheets herein. Suitable cations for such salts can be selected from potassium, sodium, ammonium, zinc, aluminium, calcium and magnesium ions, or mixtures thereof. Suitable anions associated with the aforementioned cations may be selected from chloride, citrates, sulphate, carbonate, borate and phosphate anions, or mixtures thereof.

Physical cross linking refers to polymers having cross links which are not chemical covalent bonds but are of a physical nature such that there are areas in the device having high crystallinity or areas having a high glass transition temperature. Chemical cross linking refers to polymers which are linked by chemical bonds. Preferably, the polymer is chemically cross linked by radiation techniques such as thermal-, E beam-, UV-, gamma or micro-wave radiation. In addition when chemical cross links are formed in the system, a polyfunctional cross linker and/or a free radical initiator may be present in the premix to initiate the cross linking upon irradiation. Such components can be present in quantities of up to 5% by weight.

Polymeric gellants are water soluble or water insoluble, preferably they are water soluble. Alternatively, they can be non-water soluble polymeric gellants comprising silicone materials e.g. organopolysiloxane resins, or block co-polymer thermoplastic elastomers. A more detailed description of water insoluble polymeric gellants can be found in co-pending PCT application no. PCT/US99/15201 incorporated herein by reference in its entirety.

The water-soluble polymeric gellants for use in the present invention are selected from synthetic or natural polymers, and mixtures thereof. In general, the pre-formed, gel sheets of the present invention comprise less than 50%, more preferably less than 30% and especially less than 20% by total weight of a water-soluble polymeric gellant. Suitable synthetic polymers for use herein include non-ionic water-soluble polymers, acrylic acid based polymers, cellulose derivatives, and mixtures thereof. Many materials of this type are known in the art and exemplary materials are to be found in co-pending PCT application no. PCT/US99/15201.

A particularly preferred synthetic polymer system is disclosed in WO 00/06215, incorporated herein by reference, which describes a product suitable for attaching biomedical devices to the skin. In particular the document discloses a bioadhesive, hydrogel composition comprising an aqueous plasticiser, a polymer of one or more monomers comprising a hydrophilic unsaturated water soluble acrylamido monomer, particularly NaAMPS, and a hydrophobic polymer, such as an ethylene/vinyl acetate copolymer.

Preferred polymers for use herein are natural polymers, including gelatin, polysaccharides, and mixtures thereof. Preferred are polysaccharides. The polysaccharides for use in the devices herein are preferably selected from red seaweed polysaccharides; glucomannans; galactomannans; fermentation polysaccharides, or derivatives thereof; brown seaweed polysaccharides; extracts of marine invertebrates; starch, or derivatives thereof; natural fruit extracts; plant fiber derivatives; kelp; natural plant exudates; and resinous gums; or mixtures thereof. When the gel sheets herein contain one or more polysaccharides as the water-soluble polymeric gelling agent(s), the sheets generally comprise less than 10%, preferably less than 7% and more preferably less than 5% by total dry weight of a polysaccharide or mixtures thereof. It is believed that low total polysaccharide levels impart an open gel structure such that the other components of the gel are not as tightly bound within the gel network and are freely available for diffusion.

When gelatin is used in the devices herein, a high-molecular weight gelatin is combined with a low-molecular weight one to control the solubility. A gelatin having a low molecular weight of 20,000 or less is poor in gelling ability.

Brown seaweed polysaccharides are isolated by extraction from various species of Phaebophyceae. Suitable brown seaweed polysaccharides for use herein include algin, alginic acid, ammonium alginate, calcium alginate, potassium alginate, sodium alginate, propylene glycol alginate, and mixtures thereof.

Red seaweed polysaccharides are isolated from marine plant species belonging to the class of Rhodophyceae. Red seaweed polysaccharides provide mechanical strength to an aqueous gel. Suitable red seaweed polysaccharides for use in the present invention include agar known in the industry under the (CTFA) trade designation as agar agar flake derived from various *Gelidium* plant species or closely related red algae commercially available as "Agar Agar 100" or "Agar Agar 150" from TIC Gums (Belcamp, Md., USA) or "Agar Agar K-100" from Gumix International Inc. (Fort Lee, N.J., USA); agarose commercially available as "Sea Plaque®" from FMC (Philadelphia, Pa., USA) and "Agarose Type 1-b" from Sigma-Aldrich Co. Ltd. (Poole, UK); carrageenan, comprising the fractions lambda-, iota- and kappa—which are the water extracts obtained from various members of the Gigartinaceae or Solieriaceae families, known in the industry under the (CTFA) trade designation as chondrus, commercially available as "Gelcarin® LA", "Seakem® 3/LCM", or "Viscarin® XLV", all from FMC (Philadelphia, Pa., USA); and furcellaran commercially available from Gum Technology Corporation (Tucson, Ariz., USA) and Continental Colloids Inc. (Chicago, Ill., USA), or mixtures thereof. Preferably, the red seaweed polysaccharide for use herein is selected from agar, agarose, kappa-carrageenan and furcellaran, or mixtures thereof.

Glucomannans are polysaccharides which comprise an essentially linear backbone of glucose and mannose residues. Glucomannans have short side branches attached to the linear backbone and acetyl groups are randomly present at the C-6 position of a sugar unit. The acetyl groups are generally found on one per six sugar units to one per twenty sugar units. Suitable glucomannans or derivatives thereof for use herein have a ratio of mannose to glucose of from about 0.2 to about 3. Preferred glucomannans for use herein include konjac mannan, which is the generic name for the flour formed from grinding the tuber root of the Amorphophallus konjac plant (elephant yam), commercially available under the trade name "Nutricol® konjac flour" from FMC (Philadelphia, Pa., USA); and deacetylated konjac mannan; or mixtures thereof.

Galactomannans are vegetable reserve polysaccharides which occur in the endosperm cells of numerous seeds of Leguminosae. The collective term "galactomannan" comprises all polysaccharides which are built up of galactose and mannose residues. Galactomannans comprise a linear backbone of (1→4)-linked β-D-mannopyranosyl units. To these rings are attached as branches, isolated galactopyranose residues by α-(1,6)-glucoside bonds. Galactomannans may in addition also contain minor amounts of other sugar residues. Suitable galactomannans for use herein are fenugreek gum; lucern; clover; locust bean gum known for example in the industry under the (CTFA) trade designation as carob bean gum, commercially available as "Seagul L" from FMC (Philadelphia, Pa., USA); tara gum commercially available from Starlight Products (Rouen, France) or Bunge Foods (Atlanta, Ga., USA); guar gum derived from the ground endosperms of *Cyamopsis tetragonolobus*, commercially available as "Burtonite V7E" from TIC Gums (Belcamp, Md., USA), "Jaguar C" from Rhone-Poulenc (Marietta, Ga., USA), or "Supercol" from Aqualon (Wilmington, Del., USA); and cassia gum commercially available from Starlight Products (Rouen, France), or mixtures thereof. Preferably, the galactomannans for use herein have an average one of every 1 to about 5 mannosyl units substituted with a (1→6)-linked-α-D-galactopyranosyl unit and are selected from guar gum, locust bean gum and cassia gum, or mixtures thereof.

Fermentation polysaccharides are polysaccharides which are commercially produced by the fermentation of microorganisms in a medium containing a carbon and nitrogen source, buffering agent, and trace elements. Suitable fermentation polysaccharides or derivatives thereof, for use in the present invention include gellan gum known in the industry under the (CTFA) trade designation as gum gellan, a high molecular weight hetero polysaccharide gum produced by a pure-culture fermentation of a carbohydrate with *Pseudomonas elodea*, commercially available as "Kelcogel" from Kelco (San Diego, Calif., USA); xanthan gum which is a high molecular weight hetero polysaccharide gum produced by a pure-culture fermentation of a carbohydrate with *Xanthomonas campestris*, known in the industry under the (CTFA) trade designation as xanthan, commercially available for example as "Keltrol CG 1000/BT/F/GM/RD/SF/T/TF", from Calgon (Pittsburgh, Pa., USA), or "Kelzan" from Kelco (San Diego, Calif., USA); natto gum; pullulan; rhamsan gum; curdlan; succinoglycan; welan gum; dextran, commercially available as "Sephadex G-25" from Pharmacia Fine Chemicals (Piscataway, N.J., USA) and derivatives thereof; and sclerotium gum, commercially available as "Amigel" from Alban Muller International (Montreil, France), or mixtures thereof. Preferred fermentation polysaccharides or derivatives thereof are selected from gellan gum and xanthan gum, or mixtures thereof. More preferably the fermentation polysaccharide or derivative thereof is xanthan gum.

Extracts of marine invertebrates can also be used. Polysaccharides derived from marine invertebrates, specifically the exoskeleton of such invertebrates, consist chiefly of N-acetyl-D-glucosamine residues. Examples of such polysaccharides suitable for use herein include chitosan, commercially available for example as "Marine Dew" from Ajinomoto (Teakneck, N.J., USA); and hydroxypropyl chitosan commercially available for example as "HPCH Liquid" from Ichimaru Pharcos (Yamagata Gun Gifu-Pref, Japan) and derivatives; or mixtures thereof.

Starches are polysaccharides which consist of various proportions of two glucose polymers, amylose and amylopectin. Suitable materials for use herein include starch, amylopectin and dextrin, commercially available as "Nadex 360" from National Starch (Bridgewater, N.J., USA), and derivatives or mixtures thereof. Examples of natural fruit extracts suitable for use herein include pectin, arabian and mixtures thereof. A suitable example of a plant fibre derivative for use herein is cellulose. Suitable polysaccharides obtained from natural plant exudates for use herein include karaya, tragacanth, arabic, tamarind, and ghatty gums, or mixtures thereof. Examples of resinous gums suitable for use herein include shellac gum, which is obtained from the resinous secretion of the insect *Laccifer (Tachardia) lacca*, damar gum; copal gum and rosin gum; or mixtures thereof.

Preferably, the pre-formed, unilamellar gel sheets herein comprise a mixture of water-soluble polymeric gel forming agents. The mixture is selected from one or more non-ionic water-soluble polymers; one or more acrylic acid based polymers or derivatives thereof; one or more polysaccharides; and mixtures thereof. For example, a preferred water-soluble polymeric gel forming agent mixture herein may comprise a polysaccharide and a non-ionic water-soluble polymer or, alternatively, it may comprise two polysaccharides. More preferably, the water-soluble polymeric gel forming agent is a polysaccharide mixture, wherein the polysaccharide mixture comprises (1) at least one red seaweed polysaccharide; brown seaweed polysaccharide; or mixtures thereof; and (2) at least one fermentation polysaccharide; galactomannan; glucomannan; natural plant exudate; or natural fruit extract; and derivatives or mixtures thereof. Even more preferably, the water-soluble polymeric gel forming agent of the devices of the present invention is a polysaccharide mixture comprising (1) at least one red seaweed polysaccharide; and (2) at least one fermentation polysaccharide; glucomannan; or galactomannan; and derivatives or mixtures thereof.

In a preferred embodiment, the water-soluble polymeric gel forming agent of the present invention is a polysaccharide mixture, comprising a red seaweed polysaccharide and a glucomannan or a galactomannan. The ratio of red seaweed polysaccharide to glucomannan or galactomannan in the polysaccharide mixture is preferably from about 20:1 to about 1:5 and more preferably from about 10:1 to about 1:2.

When the polymeric gel forming agents are natural in origin, the gels undergo syneresis, as herein before defined, to some degree. Syneresis provides one mechanism for the delivery of a benefit agent to a target area. The liquid layer exuded onto the surface of the coherent gel phase is readily available for diffusion, facilitating a short wear time of the device.

Hydrophilic Solvent

The gel sheets of the devices of the invention comprise at least 10% dermatologically acceptable, hydrophilic solvent. The solvent acts as a plasticiser or softener for the device, thus providing the desired mechanical properties, particularly flexibility. As used herein, a dermatologically acceptable, hydrophilic solvent is one which can be used in a sheet to be applied against the skin without causing irritation and which is miscible with water, at least in a solvent to water ratio of 1 to 10, preferably 1 to 5. A highly preferred hydrophilic solvent is water itself. Other suitable hydrophilic solvents include ethanol, propylene glycol, glycerine, sorbitol; polyethylene glycols of MW less than 30,000, preferably less than 10,000; and polypropylene glycols of MW less than 5,000, preferably less than 1,000; which can be used alone, in admixture or, preferably, in admixture with water. If necessary the solvents may be warmed to liquefy them. The use of the hydrophilic solvent not only helps to provide the desired mechanical properties to the device but can assist in diffusion of benefit agents to the skin and, by evaporation from the gel sheet, can also provide cooling, making the device more comfortable to wear. Preferred in this latter respect are solvents which are liquid at 25° C., more preferably less than 20% by weight of a solvent mixture is comprised of solvents which are solid at 25° C. Particularly preferred hydrophilic solvents are water, ethanol, propylene glycol and mixtures thereof. The total hydrophilic solvent content of the gel sheet is preferably from about 15% to about 99%, more preferably from about 20% to about 95%, and yet more preferably from about 50% to about 90% by weight of the gel sheet. Preferred gel sheets comprise more than about 10% water, more preferably more than about 30% water.

Coating Compositions

In the pre-formed device of the present invention, the first surface is at least partially coated with a discrete coating composition comprising at least one benefit agent for the skin, hair or nails. By "discrete" coating composition is meant one that is applied to the gel sheet as a distinctly different composition, in particular one having a different chemical constitution which is separately prepared from the gel sheet and is laid down as a separate layer, before, after or at the same time as the formation of the gel sheet. The coating composition allows more efficient delivery of benefit agents to the skin and affords greater formulation flexibility.

Use of the singular of "coating composition" herein is not intended to include two or more coating compositions applied to different parts of the same gel sheet. In particular it is envisaged that for a device such as a face mask, a composition suitable for oily skin may be applied to a portion of the device intended to contact the so-called 'T-zone' and a different composition suitable for dry skin may be applied to another area of the mask intended to contact the cheeks for example. More generally the coating may comprise two or more areas of different composition to suit different areas of the skin hair or nails. Alternatively the coating may be applied in two or more layers of different composition to provide for sequential release of ingredients. Preferably however, a single uniform composition is applied. References herein to 'coating composition' are intended to cover either uniform or heterogeneous compositions. Generally, the coating composition covers at least about 20%, preferably at least about 50%, more preferably at least about 75% of the area of the first surface. The coating composition can assist in adhering the patch to the skin, in which case it can be appropriate for the entire first surface to be coated with the coating composition. Alternately, there can be an area of the first surface, such as a peripheral rim, optionally with some areas in the central portion of the first surface, which is left uncoated, for the purpose of easier or less messy handling of the device or for assisting adhesion of the device to a target area of the skin, hair or nails.

The coating composition can be solid, such as a powder, or a liquid, including gels. Preferably the coating composition is a liquid, and particularly a liquid having a viscosity greater than about 1000 mPa·s, preferably greater than about 5,000 mPa·s, more preferably greater than about 7,000 mPa·s as measured on a Brookfield viscometer using a heliopath T-bar C spindle at 5 rpm.

Liquid coating compositions can be aqueous solutions, including gels, or emulsions such as oil-in-water emulsions, water-in-oil emulsions or multiple emulsions having aqueous or oily external phases. In preferred embodiments herein the coating composition is an oil-in-water emulsion having one or more internal oil phases which can include a silicone oil phase.

The weight ratio of the coating to the gel sheet is generally in the range from about 1:100 to about 2:1, preferably from about 1:25 to about 1:1, more preferably from about 1:15 to about 1:2. Preferred dosage rates of the coating compositions on the gel patch can alternatively be expressed as from about 0.001 to about 0.2 gcm$^{-2}$, preferably from about 0.005 to about 0.05 gcm$^{-2}$.

The coating composition comprises at least one benefit agent for the skin, hair or nails. Such benefit agents can be unique to the coating composition or the same as benefit agents which may be present in the gel sheet. Preferably, the gel sheet and the coating composition each comprise at least one skin benefit agent in common. In this way, whilst the coating composition can rapidly provide a benefit agent to the target area, the gel sheet can act as a reservoir for the benefit agent or inhibit the gel sheet from absorbing the benefit agent from the coating composition.

Benefit Agents

An essential characteristic of the pre-formed device of the present invention is that the coating composition comprises at least one benefit agent for the skin hair, or nails. The solid gel sheet preferably also comprises one or more of such benefit agents. The term "benefit agent" as used herein, means an active ingredient which provides a cosmetic and/or therapeutic effect to the area of application. Included in this definition of benefit agents are the categories listed below as well as, for example, vitamins, and humectants.

The benefit agents are used in a safe and effective amount, by which is meant an amount high enough to deliver the desired skin, hair or nail benefit but low enough to avoid serious side effects, at a reasonable benefit to risk ratio within the scope of sound medical judgement. The amount by weight of the benefit agent will vary with the specific agent, the ability of the agent to penetrate through the skin or into, or onto the hair and/or nails, the user's age, the user's health condition, and the condition of the skin, hair or nails of the user, and other like factors.

Benefit agents herein include their pharmaceutically-acceptable salts, by which is meant any of the commonly-used salts that are suitable for use in contact with human tissues without undue toxicity, irritation, incompatibility, allergic response, and the like.

In general, the coating compositions of the present invention comprise from about 0.01% to about 60%, preferably from about 0.1% to about 40% and most preferably from about 0.5% to about 30% by weight of the coating compositions of at least one benefit agent, or mixtures thereof.

The benefit agents useful herein can be categorised by their cosmetic or therapeutic benefit or their postulated mode of action. However, it is to be understood that they can in some instances provide more than one cosmetic or therapeutic benefit or operate via more than one mode of action. Therefore, classifications herein are made for the sake of convenience and are not intended to limit the benefit agent to that particular application or applications listed. The following exemplary benefit agents are useful in the device of the present invention.

A more complete listing of benefit agents can be found in WO98/18444 and co-pending PCT application no. PCT/US99/15202, both of which are incorporated herein by reference.

Anti-Acne Actives: Anti-acne actives can be effective in treating and preventing acne vulgaris, a chronic disorder of the pilosebaceous follicles. Preferred anti-acne actives include benzoyl peroxide, lactic acid, 4-methoxysalicylic acid, metronidazole, niacinamide, panthenol, retinoic acid and derivatives thereof, salicylic acid, sulphur, triclosan, zinc oxide, and mixtures thereof.

Emollients: Examples of emollients useful herein include mineral oil, petrolatum, $C_7$-$C_{40}$ branched chain hydrocarbons, $C_1$-$C_{30}$ alcohol esters of $C_1$-$C_{30}$ carboxylic acids, monoglycerides of $C_1$-$C_{30}$ carboxylic acids, $C_1$-$C_{30}$ carboxylic acid monoesters and polyesters of sugars, for example, sefa cottonate (sucrose polycottonseedate), polydialkylsiloxanes; silicone gums, resins and elastomers; cyclomethicones having 3 to 9 silicon atoms, vegetable oils, hydrogenated vegetable oils and mixtures thereof. Preferred emollients are selected from linear and branched chain hydrocarbons, sugar polyesters and silicones, especially dimethicone and dimethiconol.

Non-Steroidal Anti-Inflammatory Actives (NSAIDS): Examples of suitable NSAIDS and their esters for use herein are described in WO98/18444.

Topical Anaesthetics: Examples of suitable topical anaesthetic drugs for use herein are benzocaine and bupivacaine.

Artificial Tanning Agents and Accelerators: Artificial tanning agents can help in simulating a natural suntan by increasing melanin in the skin or by producing the appearance of increased melanin in the skin. Non-limiting examples of artificial tanning agents and accelerators include dihydroxyacetone, glucose tyrosinate and acetyl tyrosine, brazilin, caffeine, coffee extracts, DNA fragments, isobutyl methyl xanthine, methyl xanthine, PHOTOTAN (available from Laboratoires Serobiologiques located in Somerville, N.J.), prostaglandins, tea extracts, theophylline, UNIPERTAN P2002 (available from Unichem, located in Chicago, Ill.) and UNIPERTAN P27 (available from Unichem, located in Chicago, Ill.); and mixtures thereof.

Antiseptics: Suitable antiseptics for use herein include alcohols, benzoate, sorbic acid, and mixtures thereof.

Anti-microbial and Anti-fungal Actives: Anti-microbial and anti-fungal actives can be effective to prevent the proliferation and growth of bacteria and fungi. Non-limiting examples of antimicrobial and antifungal actives include ketoconazole, benzoyl peroxide, tetracycline, benzalkonium chloride, benzoic acid and its salts, butyl paraben, cinnamon oil, citronella oil, echinacea, ethyl paraben, GLYDANT PLUS (available from Lonza located in Fairlawn, N.J.), grapefruit seed oil, iodopropynl butyl carbamide lemon balm oil, salicylic acid, sodium metabisulphite, sodium sulphite, sorbic acid and its salts, and tea tree oil.

Skin Soothing Agents: Skin soothing agents can be effective in preventing or treating inflammation of the skin. The soothing agent enhances the skin appearance benefits of the present invention, e.g., such agents contribute to a more uniform and acceptable skin tone or colour. Examples of skin soothing agents include allantoin, aloe, bisabolol, borage oil, chamomile, evening primrose, panthenol, and tocopherol.

Sunscreening Agents: Sunscreens useful herein include both inorganic sunscreens such as titanium and zinc oxides, as well as the many commercially available UVA and UVB absorbing organic sunscreens.

Skin Barrier Repair Aids: Skin barrier repair actives are those skin care actives which can help repair and replenish the natural moisture barrier function of the epidermis. Non-limiting examples of skin barrier repair aids include ceramides, cholesterol, lanolin, lanolin alcohols, n-acetyl cysteine, n-acetyl-L-serine, niacinamide, nicotinic acid and its esters, nicotinyl alcohol, panthenol, phosphodiesterase inhibitors, trimethyl glycine, tocopheryl nicotinate, and vitamin D3 and analogs or derivatives.

Anti-Wrinkle and Anti-Skin Atrophy Actives: Anti-wrinkle and anti-skin atrophy actives can be effective in replenishing or rejuvenating the epidermal and/or dermal layer. These actives generally provide these desirable skin care benefits by promoting or maintaining the natural process of desquamation and/or building skin matrix components (e.g., collagen and glycosaminoglycans). Examples of anti-wrinkle and anti-skin atrophy actives include niacinamide, nicotinic acid and its esters, nicotinyl alcohol, estrogens and estrogenic compounds, or mixtures thereof.

Skin Repair Actives: Skin repair actives can be effective in repairing the epidermal and/or dermal layer. Non-limiting examples of skin repair actives include adenosine, aloe derived lectins, ascorbyl palmitate, azaleic acid, biotin, blackberry bark extract, catecholamines, chalcones, cis retinoic acid, citric acid esters, coenzyme Q10 (ubiquinone), dehydrocholesterol, dehydroepiandrosterone, dehydroascorbic acid and derivatives thereof, dehydroepiandrosterone sulphate, estrogen and its derivatives, farnesol, gingko bilboa extracts, ginseng extracts, lactate dehydrogenase inhibitors, magnesium ascorbyl phosphate, melatonin, N-acetyl cysteine, pantethine, phytic acid and its salts, retinal, retinol, retinyl acetate, retinyl propionate and vitamin K.

Lipids: Examples of suitable lipids include cetyl ricinoleate and phytanetriol.

Skin Lightening Agents: Skin lightening agents can actually decrease the amount of melanin in the skin or provide such an effect by other mechanisms. Skin lightening agents suitable for use herein are described in EP-A-758,882 and EP-A-748,307, both of which are incorporated herein by reference. Other skin lightening agents include arbutin, ascorbic acid, ascorbyl palmitate, azelaic acid, butyl hydroxy anisole, gallic acid and its derivatives, glycyrrhizinic acid, hydroquinine, inositol ascorbate, kojic acid, niacinamide and vitamin $D_3$ and its analogues.

Sebum Inhibitors: Sebum inhibitors can decrease the production of sebum in the sebaceous glands. Examples of suitable sebum inhibitors include dichlorophenyl imidazoldioxolan, aluminium hydroxy chloride, corticosteroids and cucumber extracts.

Sebum Stimulators: Sebum stimulators can increase the production of sebum by the sebaceous glands. Non-limiting examples of sebum stimulators include bryonolic acid, dehydroepiandrosterone and orizanol.

Skin Sensates: Non-limiting examples of suitable skin sensates for use herein include agents which impart a cool feel such as camphor, thymol, 1-menthol and derivatives thereof, eucalyptus, carboxamides; menthane ethers and menthane esters; and agents imparting a warm feel such as cayenne tincture, cayenne extract, cayenne powder, vanillylamide nonanoate, nicotinic acid derivatives (benzyl nicotinate, methyl nicotinate, phenyl nicotinate, etc.), capsaicin, nasturtium officinale extract, *Zanthoxylum piperitum* extract and ginger extract, or mixtures thereof.

Protease Inhibitors: Protease inhibitors are compounds which inhibit the process of proteolysis, that is, the splitting of proteins into smaller peptide fractions and amino acids. Examples of suitable protease inhibitors include A E COMPLEX (available from Barnet Products located in Englewood, N.J.), BLUE ALGAE EXTRACT (available from Collaborative Labs Inc. located in East Setauket, N.Y.), and SEPICONTROL AS (available from Seppic located in Paris, France).

Skin Tightening Agents: Examples of skin tightening agents include sodium polystyrene sulphonate, BIOCARE SA (available from Amerchol located in Edison, N.J.) and egg albumen.

Anti-Itch Ingredients: Examples of anti-itch ingredients include ichthyol and OXYGENATED GLYCERYL TRIESTERS (available from Laboratoires Seporgia located in Sophia Antipolis, France.)

Hair Growth Inhibitors: Suitable agents for inhibiting hair growth include 17 beta estradiol, anti angiogenic steroids, curcuma extract, cycloxygenase inhibitors, evening primrose oil, linoleic acid and 5-alpha reductase inhibitors such as ethynylestradiol and, genistine.

Desquamation Enzyme Enhancers: These agents enhance the activity of endogenous desquamating enzymes. Non-limiting examples of desquamation enzyme enhancers include N-methyl serine, serine, trimethyl glycine, and mixtures thereof.

Anti-Glycation Agents: Anti-glycation agents prevent the sugar induced crosslinking of collagen. A suitable example of an anti-glycation agent includes AMADORINE (available from Barnet Products Distributor located in Englewood, N.J.).

Preferred examples of benefit agents useful herein include those selected from the group consisting of ascorbic acid and derivatives thereof, salicylic acid, niacinamide, panthenol, tocopheryl nicotinate, benzoyl peroxide, 3-hydroxy benzoic acid, flavonoids (e.g., flavanone, chalcone), farnesol, phytantriol, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, retinyl esters (e.g., retinyl propionate), phytic acid, N-acetyl-L-cysteine, lipoic acid, tocopherol and its esters (e.g., tocopheryl acetate), azelaic acid, arachidonic acid, tetracycline, ibuprofen, naproxen, ketoprofen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neomycin sulfate, theophylline, and mixtures thereof.

For cosmetic methods of treatment of the skin, hair or nails, the cosmetic benefit agent is preferably selected from anti-wrinkle and anti-skin atrophy actives, anti-acne actives, artificial tanning agents and accelerators, emollients, humectants, skin repair actives, skin barrier repair aids, skin lightening agents, skin sensates, skin soothing agents, lipids, sebum inhibitors, sebum stimulators, sunscreening agents, protease inhibitors, skin tightening agents, anti-itch ingredients, and desquamation enzyme enhancers, or mixtures thereof.

Humectants

Preferred coating compositions and gel sheets comprise at least one humectant. Humectants increase the moisturising characteristics of the device when applied to the target surface. Some humectants, such as glycerine, can also act as a solvent to plasticise the gel sheet. Certain humectants, such as hexylene glycol, may also contribute to the antibacterial properties of a pre-formed device of the present invention.

Suitable humectants for use in the present invention are described in WO98/22085, WO98/18444 and WO97/01326, all of which are incorporated herein by reference. Preferably, the humectants for use herein are selected from glycerine, butylene glycol, hexylene glycol, panthenol, polyethylene glycol, and mixtures thereof.

In general, the coating compositions and gel sheets of the present invention comprise from about 1.0% to about 50%, preferably from about 5% to about 45%, more preferably from about 10% to about 40% by weight of a humectant.

Emulsifiers/Surfactants

The gel sheets and coating compositions of the present invention optionally comprise one or more surfactants and/or emulsifiers. Emulsifiers and/or surfactants, generally help to disperse and suspend a discontinuous phase within a continuous phase. A surfactant may also be useful if the product is intended for skin, hair or nail cleansing. For convenience hereinafter emulsifiers will be referred to under the term 'surfactants', thus 'surfactant(s)' will be used to refer to surface active agents whether used as emulsifiers or for other surfactant purposes such as skin, hair or nail cleansing. Known or conventional surfactants can be used in the composition, provided that the selected agent is chemically and physically compatible with essential components of the composition, and provides the desired characteristics. Suitable surfactants include silicone materials, non-silicone materials, and mixtures thereof.

The compositions of the present invention preferably comprise from about 0.01% to about 15% of a surfactant or mixture of surfactants. The exact surfactant or surfactant mixture chosen will depend upon the pH of the composition and the other components present. Preferred surfactants are nonionic.

Among nonionic surfactants useful herein are condensation products of alkylene oxides with fatty acids (i.e. alkylene oxide esters of fatty acids); the condensation products of alkylene oxides with 2 moles of fatty acids (i.e. alkylene oxide diesters of fatty acids); the condensation products of alkylene oxides with fatty alcohols, examples of which include PEG 40 hydrogenated castor oil, steareth-2, isoceteth-20, and oleth-20. Still other nonionic surfactants are the condensation products of alkylene oxides with both fatty acids and fatty alcohols [i.e. wherein the polyalkylene oxide portion is esterified on one end with a fatty acid and etherified on the other end with a fatty alcohol].

Other nonionic surfactants that are useful herein are alkyl glucosides and alkyl polyglucosides, described in more detail in WO98/18444. Still other useful nonionic surfactants include polyhydroxy fatty acid amide surfactants, described in WO98/04241.

Other nonionic surfactants suitable for use herein include optionally alkoxylated sugar esters and polyesters, fatty acid amides.

Preferred nonionic surfactants are those selected from the group consisting of laureth-4, laureth-23, ceteareth-12, sucrose cocoate, steareth-100, polysorbate 60, PEG-60 hydrogenated castor oil, isoceteth-20, oleth-20, PEG-100 stearate, and mixtures thereof.

Other emulsifiers useful herein are fatty acid ester blends based on a mixture of sorbitan or sorbitol fatty acid ester and sucrose fatty acid ester, as described in more detail in WO98/22085, incorporated by reference herein.

Hydrophilic surfactants useful herein can alternatively or additionally include any of a wide variety of cationic, anionic, zwitterionic, and amphoteric surfactants such as are known in the art. See, e.g., McCutcheon's, Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety.

A wide variety of cationic surfactants are useful herein. Suitable cationic surfactants for use herein are disclosed in WO98/18444. Exemplary anionic surfactants include the alkoyl isethionates (e.g., $C_{12}$-$C_{30}$), alkyl and alkyl ether sulfates and salts thereof, alkyl and alkyl ether phosphates and salts thereof, alkyl methyl taurates (e.g., $C_{12}$-$C_{30}$), and soaps (e.g., alkali metal salts, e.g., sodium or potassium salts) of fatty acids. Examples of amphoteric and zwitterionic surfactants include betaines, sultaines, hydroxysultaines, alkyl sarcosinates (e.g., $C_{12}$-$C_{30}$), and alkanoyl sarcosinates.

The gel sheets and coating compositions of the device of the present invention may optionally contain a silicone containing emulsifier or surfactant. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain $C_2$-$C_{30}$ pendant side chains. Still other useful dimethicone copolyols include materials having various cationic, anionic, amphoteric, and zwitterionic pendant moieties.

Other Optional Ingredients

The devices of the present invention can comprise a wide range of other optional components. These additional components should be dermatologically acceptable. The CTFA Cosmetic Ingredient Handbook: Second Edition, 1992, which is incorporated by reference herein in its entirety, describes a wide variety of non-limiting cosmetic and pharmaceutical ingredients commonly used in the cosmetic industry, which are suitable for use in the compositions of the present invention. Non-limiting examples of functional classes of ingredients are described at page 537 of this reference. Examples of these and other functional classes include: absorbents, antibiotics, anti-dandruff agents, anti-perspirant agents, antioxidants, biological additives, bleach activators, brighteners, buffering agents, chelating agents, chemical additives, colorants, cosmetics, cleansers, deodorants, desquamation actives, depilatories, drug astringents, dyes, dye transfer agents, enzymes, external analgesics, film formers, fragrance components, insect repellants, fungicides, opacifying agents, oxidative dyes, oxidising agents, pest control ingredients, pH adjusters, pH buffers, pharmaceutical actives, preservatives, radical scavengers, skin, hair or nail bleaching agents, skin, hair or nail conditioners, skin, hair or nail penetration enhancers, stabilisers, surface conditioners, reducing agents, temperature depressors, and warmth generators.

Also useful herein are aesthetic components such as colourings, essential oils, and skin, hair or nail healing agents.

Other optional materials herein include pigments and other particulates which may provide visual or skin-feel benefits. Pigments suitable for use in the compositions of the present invention can be organic and/or inorganic. Also included within the term pigment are materials having a low colour or lustre such as matte finishing agents, and also light scattering agents. Examples of suitable pigments are iron oxides, acylglutamate iron oxides, titanium dioxide, ultramarine blue, D&C dyes, carmine, and mixtures thereof. Depending upon the type of composition, a mixture of pigments will normally be used. Other particulates useful herein include nylon-12, polymethylsilsesquioxane and dimethicone/vinyl dimethicone cross polymer.

The pH of the gel sheets and coating compositions herein is preferably from about 3 to about 9, more preferably from about 4 to about 8.

Methods of Producing the Gel Sheet

The gel sheets are formed by subjecting a mixture of the one or more gelling agents and hydrophilic solvent, together with any additional additives such as plasticisers or benefit agents, to a gelling step, thereby forming a gel sheet which is self-supporting. The nature of the gelling step depends on the nature of the gelling agent(s) used. For example, it may involve the addition of metal ions to cross-link a polymer solution or it may involve irradiation with ultraviolet rays to produce a self-supporting gel.

In many cases, the gelling step is achieved via cooling. This involves heating and mixing the solvent and gelling agent(s), and any other optional ingredients, to a first temperature above the gel point of the mixture; placing the mixture in a suitably shaped mould; and gelling the gel-forming mixture at a second temperature, which is below the first temperature and at or below the gel point of the mixture to produce a solid gel sheet. Alternatively, the mixture can be made directly in a mould.

In forming the gel sheet, its components can be added simultaneously or sequentially in any order. The order of adding the components may depend on the properties and characteristics thereof. Preferably, the gelling agent(s) and any benefit agents are sufficiently dissolved in the solvent before any other components are added. By "sufficiently dissolved" is meant that the mixture appears substantially or completely transparent. The temperature of the mixture is usually maintained above the gel point until all of the components are added. In some cases, it may be beneficial to begin to lower the temperature of the mixture prior to adding certain components.

In a preferred embodiment, the gel sheet is produced via injection moulding. It is believed that the sheet so produced is stronger due to the smoother finish of the surface, which provides a greater resistance to tearing. An injection moulding process for producing a gel sheet comprises the steps of injecting a gel-forming mixture into a suitably shaped mould, the mixture being maintained prior to the injection step at a first temperature above the gel point of the gel-forming mixture; and cooling the gel-forming mixture in the suitably shaped mould to a second temperature below the gel point of the gel-forming mixture, to form a solid sheet. Prior to gelling, the mixture is kept fluid enough to enable it to be readily supplied to a die by any conventional means, in addition to injection moulding processes. Lubricants can be added to assist in feeding the gel-forming mixture along the bore of an extruding barrel.

Gel-forming mixtures can be supplied to a suitably shaped mould by any well known technique including gravity feed systems and pneumatic or mechanical injection systems. Injection moulding is the most preferred technique because of the fluidity and low processing temperatures of the mixtures. A very wide range of moulding pressures may be employed. Generally, the moulding pressure is between about 0.1 to about 5 MPa (about 1 to about 50 atmospheres), although higher or lower pressures may be employed depending on the moulding technique used.

When gelling is achieved via cooling, the moulding temperature must, of course, be at or below the gel point of the gel-forming mixture in order to produce a solid sheet. The appropriate mould temperature can be achieved before, during, or after the mixture is supplied to the mould. After the sheet is moulded and cooled to a temperature below the gel point, the sheet is removed from the mould. The sheet requires no special handling during removal from the mould.

In a gel sheet which has a non-planar topography on at least one, preferably both of the first and second surfaces, the mould has corresponding surfaces which are the negative image of first and second surfaces of the sheet itself. The non-planar topography is of a freely selectable shape. If the non-planar topography has periodicity, the corresponding mould surface has negative image of the same periodicity.

A preferred method of producing a device according to the invention comprises the steps of:
a) providing the solid gel sheet;
b) at least partially coating the first surface thereof with a coating composition comprising at least one skin benefit agent; and
c) packaging the coated gel sheet in a sealed, protective wrapper.

The device as packaged can optionally be provided with a release liner to help prevent the device from drying out or to improve handling. A release liner is removed before use.

Substrates

The pre-formed devices of the present invention do not require supporting or strengthening by an occlusive or non-occlusive backing material, often referred to as a substrate. However, a substrate, intended to be a part of the device as worn by a user, can be combined with the gel sheet and would confer further support or strengthening. In addition, substrates may also be employed to make the devices more pleasant or easier to handle in instances where the device is wet or sticky to the touch; to prevent evaporation of active ingredients; or to act as a means for adhering a device to the skin when an adhesive is coated around its periphery. A substrate may be impregnated with, or adhered or laminated to one surface of the device. A substrate is particularly useful when the device according has a large surface area, such as a whole face mask.

If the substrate is to be used to confer further support or strengthening, the substrate will be sufficiently compatible with the device of the present invention, so as not to delaminate from the device. There can be difficulties in matching a substrate with the gel sheet. Combining a flexible substrate with a flexible gel does not necessarily produce a flexible patch or mask device. Aside from the problem of delamination, many flexible substrates often display a degree of porosity such that the wet gel infiltrates the substrate and forms strong gel networks within its fibres. Such networks may reduce the flexibility of the resultant device. Further, the substrate may not provide a patch or mask device with an unobtrusive appearance on the skin, hair, or nails. This will often depend on the choice of substrate and its characteristics.

A wide variety of materials can, however, be used as the substrate. The following characteristics are desirable: (i) sufficient wet strength for use, (ii) sufficient flexibility, (iii) sufficient loft and porosity, (iv) sufficient hydrophilicity such that the gel mixture may diffuse and infiltrate into the substrate, (v) sufficient compatibility with the mixture to prevent de-lamination, (vi) sufficient transparency or translucency, and (vii) appropriate size. Preferably the substrate is non-occlusive. Suitable substrate classes meeting the above criteria include woven and non-woven materials; polymeric sheet materials such as formed films; and paper substrates.

Alternatively, substrate like materials may be used as a texturing surface. If such a substrate like material is to be used as a texturing surface, it will, preferably, delaminate easily from the device, in the same way as a release liner.

Methods of Use

Following application of a device to a target area of the skin hair or nails, the device will generally be left on the target area for at least 1 minute, preferably at least 5 minutes, it can be left on for a period of up to 12 hours, preferably up to 3 hours, more preferably up to 1 hour, though most preferably for less than 15 minutes. The device can then be removed in one piece.

Depending on the benefit agent (or benefit agents) contained therein, the pre-formed, devices of the present invention may have at least one of the following uses; hydrating the skin, hair or nails, smoothing fine lines and wrinkles; cosmetically treating acne; firming the skin, strengthening; softening; exfoliating; improving and/or evening skin tone and/or texture; skin, hair or nail lightening; tanning; reducing the appearance of pores; absorbing or controlling secretions; protecting and/or soothing the skin, hair or nails, muscles, aches or pains; reducing puffiness, and/or dark circles; stimulating wound healing; warming, refreshing or cooling the skin, hair or nails; relieving inflammation; brightening the complexion; decongesting; reducing swelling; treating dermatological conditions; cushioning; purifying; fragrancing; reducing bacterial or micro-organism growth; healing; repelling insects; removing unwanted hair, dirt, or make-up; and colouring or bleaching the target area to which the device is applied. Preferably, the pre-formed devices herein are cosmetically used for hydrating the skin, hair or nails; smoothing fine lines and wrinkles; and improving and/or evening the skin tone and/or texture.

EXAMPLES

The invention is illustrated by the following examples.

| | Gel Sheet Examples 1–4 | | | |
|---|---|---|---|---|
| Ingredient | 1 % w/w | 2 % w/w | 3 % w/w | 4 % w/w |
| Agarose | 0.3 | 0.8 | 1.6 | 1.5 |
| Agar | 0.60 | — | — | — |
| Kelgum (Kelco)[1] | — | 0.5 | 0.8 | 0.75 |
| Keltrol T (Kelco)[1] | 0.2 | — | — | — |
| Locust Bean Gum | 0.2 | — | — | — |
| Niacinamide | — | 5.0 | 8.0 | 10.0 |
| D-Panthenol | 5.0 | — | 2.0 | 1.0 |
| Glycerin | 10.0 | 15.0 | 10.0 | 10.0 |
| Disodium EDTA | — | 0.10 | 0.10 | 0.10 |
| Butylene Glycol | — | 5.0 | — | — |
| Hexylene Glycol | 3.0 | — | 5.0 | 5.0 |
| Ethyl Paraben | 0.20 | 0.15 | 0.15 | 0.15 |
| Water | to 100% | to 100% | to 100% | to 100% |

[1]Kelgum ™ and Keltrol ™ T are respectively a 1:1 mixture of xanthan gum and locust bean gum; and xanthan gum, supplied by Kelco, San Diego, CA, USA.

The polysaccharide gums are mixed with water to form a uniformly dispersed mixture (this can be facilitated by pre-dispersing the polysaccharides in a non-solvent e.g. polyhydric alcohol) and any additional components are added. The mixture is heated with stirring to a first temperature above the gel point of the mixture (ca. 90° C.) to fully hydrate the polysaccharide gums. The liquid gel is then dispensed into a suitably shaped mould. Injection moulding is the preferred dispensing method. This eliminates any defects which may be introduced by cutting the gel and so improves the robustness of the sheet. Injection moulding also allows the sheet to be readily formed into a three-dimensional structure. The liquid gel is then cooled to a second temperature cooler than the first temperature at or below the gel point of the mixture (ambient temperature) to set up the gel structure. The sheet may then be removed from the mould and coated with a coating compositions shown below.

If a substrate is to be used, this may be placed in the suitably shaped mould prior to dispensing the gel or it may be placed on the surface of the liquid gel during the cooling stage.

In some compositions, metal ions (e.g. $Ca^{2+}$, $K^+$) may be included in the formulation to increase the gel strength of the sheet. In this case, the metal ions are added in the form of an aqueous solution and are stirred into the liquid gel immediately before the dispensing step.

The above method may be modified as necessary depending on the nature of any additional components. For example, if non-aqueous components are present, the liquid gel may be homogenised immediately prior to moulding or casting to ensure dispersion of the non-aqueous components. Similarly, if heat sensitive ingredients are incorporated, the formulation should be cooled to an appropriate temperature (dependent on the ingredient) after the gum hydration step and the heat sensitive ingredient added at this stage.

The liquid gel may be de-gassed, e.g. by vacuum, to remove air bubbles dispersed within the liquid. This de-gassing step, if followed, would be the final step immediately prior to dispensing the liquid gel.

Other, suitable gel sheets can be prepared by following the Examples 1-15 of WO 00/06215.

| Coating composition: Examples 6–10 | | | | | |
| --- | --- | --- | --- | --- | --- |
| Ingredient | 6 % w/w | 7 % w/w | 8 % w/w | 9 % w/w | 10 % w/w |
| Kelgum ™ (see above) | 0.1 | — | — | — | — |
| Keltrol ™ T (see above) | — | 0.5 | 0.9 | — | 0.8 |
| Locust bean gum | 0.4 | — | — | — | — |
| Polyacrylamide, isoparaffin & laureth-7 | — | — | — | 2.75 | — |
| Niacinamide | 5.0 | — | 8.0 | 3.5 | 10.0 |
| D-Panthenol | — | 5.0 | 2.0 | 2.0 | 1.0 |
| Glycerin | — | 5.0 | 10.0 | 9.0 | 10.0 |
| Disodium EDTA | 0.10 | 0.1 | 0.1 | 0.1 | 0.1 |
| Butylene glycol | — | 5.0 | — | — | — |
| Hexylene glycol | — | — | 5.0 | — | 5.0 |
| Tospearl ™ 145[2] | — | — | 6.0 | 1.0 | 7.5 |
| DC 2-1559 emulsion[3] | — | — | 3.0 | 4.0 | 3.0 |
| Magnesium ascorbyl phosphate | 3.0 | — | — | — | — |
| Tocopheryl acetate | 0.5 | — | — | 0.75 | — |
| PEG-60 hydrogenated castor oil | 1.50 | — | — | — | — |
| Cetyl alcohol | — | — | — | 1.5 | — |
| Stearyl alcohol | — | — | — | 1.0 | — |
| Lonzaine ™ 16SP[4] | 0.47 | — | — | — | — |
| Tinoderm ™ E[5] | — | — | — | — | 10.0 |
| Sucrose cocoate and sorbitan stearate[6] | — | — | — | 1.0 | — |
| Isohexadecane | — | — | — | 2.0 | — |
| Isopropyl isostearate | — | — | — | 1.0 | — |
| SEFA cottonate | — | — | — | 1.0 | — |
| Petrolatum | — | — | — | 3.0 | — |
| Water, fragrance, preservatives | to 100% | | | | |

[2]Polymethylsilsesquioxane from Toshiba
[3]Dimethicone, dimethiconol, laureth-4, laureth-23, and water; from Dow Corning
[4]Water and cetyl betaine from Lonza
[5]Water, tocopheryl acetate, polysorbate 80, caprylic/capric triglyceride and lecithin from CIBA
[6]Arlatone 2121 from ICI The making method for the coating composition depends on the nature of the composition e.g. aqueous solution, o/w emulsion etc. and would follow procedures known to those skilled in the art. The gums are pre-dispersed in a non-solvent for the gums (e.g. polyhydric alcohol) and then dispersed in a portion of the water phase. The water soluble components (e.g. niacinamide, panthenol) are dissolved in a portion of the water phase and the thickener premix is then added, with stirring, to produce a thickened coating composition. Heating may be necessary to ensure complete dissolution of sparingly soluble components (e.g. ethyl paraben) or to ensure complete hydration of the thickening agents. Components which are not water soluble (e.g. tocopheryl acetate) may be pre-dispersed in a solubilising agent (e.g. PEG-60 hydrogenated castor oil) prior to addition to the coating composition). Particulate materials may be dispersed in the coating via conventional mixing techniques.

Application of Coating to the Gel Sheet

A variety of methods are suitable for applying the coating to the gel sheet in order to form the finished device. For example, the coating may be applied directly to the gel sheet e.g. dispensed via a pipette to provide 'dots' of coating or spread with a brush to provide an uniform layer. Alternatively, the coating may be applied using screen printing techniques or via an extrusion process. The coating may also be applied to the gel sheet via an indirect process. For example, the coating may be applied to a surface of the packaging material (e.g. plastic tray, release liner sheet) and then the gel sheet is placed on top of this coating layer. A variety of methods may be used to apply the coating to the packaging material. These include air atomised spraying of the coating, dot deposition of the coating via a nozzle device or an electrofluidic coating process of the type used in ink jet printing. A preferred method is dot deposition of the coating composition into a packaging tray using nozzles, swirling the nozzles to provide an uniform layer of coating, then pressing the gel sheet onto the top of the coating composition.

The devices herein are then packaged into materials which have low water vapour permeability to minimise drying out of the device during storage. Suitable packaging for devices herein include sachets or sealed trays. Any suitable material can be used for the packaging such as plastics materials and foil laminates. If the device is packaged in a sachet, it is preferably further mechanically protected prior to use. This protection can be provided by a substrate or by a release liner such as a plastic film, which provides easy release for the device.

An embodiment of the device, shown in side section is shown in FIG. 1. Device 1 comprises a gel sheet 2 and coating composition 4 on a first surface 12 of the gel sheet. The device is generally flat with a raised outer rim 18 which gives greater mechanical strength to the device on handling. In plan view the device would appear broadly crescent shaped, of dimensions such that a notional rectangle of 4 cm×2 cm bounds the crescent. The gel sheet has a second, upper surface 16 opposed to the first surface 12. The central, thinner portion 22 of the gel sheet has an average thickness of 1.2 mm and is textured on the first and second surfaces. The texturing on the first and second surfaces is of different patterns and helps to reduce shine from the patch, making it less visually apparent in use. The texturing on the first surface 12 also helps the coating 4 to adhere to the gel sheet.

Methods of Evaluation of the Devices

Device Transparency

Transparency of the device is measured by assessing the visibility of printed text through the device. The printed text is prepared by printing the English alphabet (capital letters) onto transparency film (Universal Office Supplies) using Microsoft Word Arial font and a LaserJet 4 Plus printer (Hewlett Packard) fitted with a black ink cartridge. Printed transparency films are prepared in font sizes ranging from 4 points to 28 points. The printed transparency films are then laid over white paper sheets to ensure a uniform background and all samples assessed under normal indoor lighting conditions.

A sample of the gel of interest is moulded to produce a disc of gel with a thickness (depth) of 7 mm. This gel disc is evenly coated with the coating composition at a rate of 0.015 gcm$^{-2}$ and placed, coated face uppermost, onto the transparency film printed with 4 font size. The visibility of the printed text is assessed through the disc of gel. If the text is not legible through the gel disc, the gel disc is transferred to the next largest font size print and the assessment repeated. This process is repeated until a font size is reached that is legible through the gel. The smallest font size legible through the gel sample is then assigned the "transparency threshold" for that device.

The preferred "transparency threshold" for the devices of the present invention is preferably no greater than about 10 point, preferably no greater than about 7 point and especially preferred is no greater than about 4 point.

Device Flexibility

Figure 2:
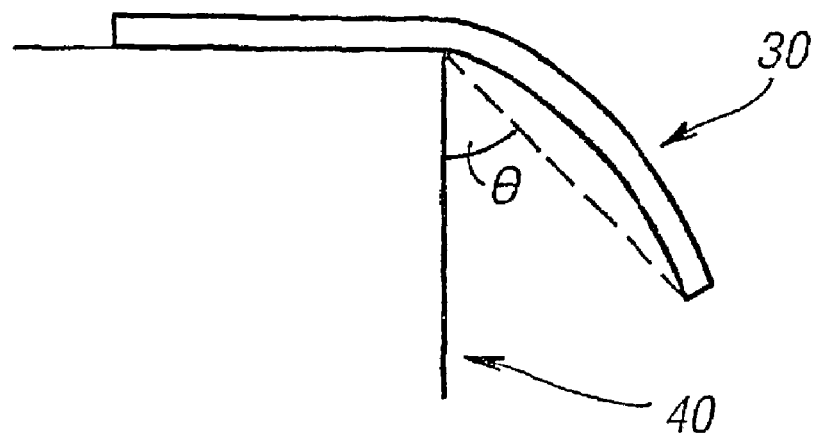
FIG. 2 is a schematic view of a set up for measuring device flexibility.

The flexibility of a device of the present invention can straightforwardly be assessed by measuring how much the device bends under its own weight when it overhangs an edge. A 4 cm by 2 cm rectangular, test strip of the material used to make the device is prepared. The strip should have a rectangular cross-section of the same thickness as the average thickness of the device of interest, the average being weighted over the area of the largest of the first and second surfaces. Although, for devices of the present invention, the flexibility is predominantly determined by the gel sheet, for the avoidance of doubt the test strip should be evenly coated with the coating composition of the device of interest at a rate of 0.015 gcm$^{-2}$. Similarly, if the device of interest includes a substrate that is intended to be part of the device as worn by a user, the test should be performed with the substrate included. The strip, coated surface uppermost, is supported on a flat surface, having a rectangular edge so that 2 cm of the 4 cm length of the strip can overhang without obstruction. The arrangement is shown schematically in FIG. 2. Gel strip 30 (coating not shown) overhangs the vertical edge of solid support 40, whose upper surface is horizontal. The angle θ of overhang from the vertical is measured by drawing a straight line (shown as a dashed line, in FIG. 2) from the tip of the gel sheet to the edge of the support. This can conveniently be done from a photograph.

The angle of overhang, θ, is the Flex Angle of the device. In general devices according to the invention should have a Flex Angle of from about 15 to about 80°, preferably from about 25 to about 75° and more preferably from about 40 to about 60°.

What is claimed is:

1. A cosmetic device for delivering benefit agents to the skin, hair or nails, the device comprising
    a) a pre-formed solid gel sheet having opposed first and second surfaces, wherein the gel sheet comprises:
        (i) one or more gelling agents,
        (ii) at least 10% dermatologically acceptable hydrophilic solvent, and
        (iii) a percentage, by weight of the gel sheet, of a first benefit agent selected from the group consisting of anti-wrinkle actives, anti-skin atrophy actives, anti-acne actives, artificial tanning agents and accelerators, skin repair actives, skin barrier repair aids, skin lightening agents, sebum inhibitors, sunscreen agents, protease inhibitors, skin tightening agents, desquamation enzyme enhancers, and mixtures thereof; and
    b) a discrete coating composition at least partially coated on the first surface of the solid gel sheet, said coating composition comprising a percentage, by weight of the coating composition, of a second benefit agent selected from the group consisting of anti-wrinkle actives, anti-skin atrophy actives, anti-acne actives, artificial tanning agents and accelerators, skin repair actives, skin barrier repair aids, skin lightening agents, sebum inhibitors, sunscreen agents, protease inhibitors, skin tightening agents, desquamation enzyme enhancers, and mixtures thereof;

wherein the first benefit agent and second benefit agent are the same, wherein the percentage of the first benefit agent is not less than the percentage of the second benefit agent, and wherein said solid gel sheet comprises a first region having a first thickness and a second region having a second thickness, wherein the first thickness is not the same as the second thickness.

2. The cosmetic device according to claim 1 wherein the coating composition is a liquid having a viscosity greater than 1000 mPa·s.

3. The cosmetic device according to claim 2 wherein the coating composition is in the form of an oil in water emulsion.

4. The cosmetic device according to claim 1 wherein the hydrophilic solvent is selected from water, ethanol, propylene glycol, glycerine, and mixtures thereof.

5. The cosmetic device according to claim 1 wherein the gel sheet is unilamellar.

6. The cosmetic device according to claim 1 which further comprises a substrate adhered to the gel sheet.

7. The cosmetic device according to claim 1 which has a transparency threshold of no greater than 10 point.

8. A method of delivering at least one benefit agent to the skin, hair or nails, the method comprising applying a device according to claim 1 to a target area of the skin, hair or nails so that the coated first surface is in contact with the target area, and leaving the device at the target area for a period of from 1 minute to 12 hours.

9. The cosmetic device according to claim 1 wherein the first surface or second surface comprises a textured pattern.

10. The cosmetic device according to claim 1 wherein the textured pattern is sinusoidal, saw-tooth, or conical.

11. The cosmetic device according to claim 1 wherein the first region is a central portion and the second region is an outer rim.

12. The cosmetic device according to claim 1 wherein the coating composition is in the form of an aqueous solution.

13. The cosmetic device according to claim 1 wherein the percentage of the first benefit agent is greater than the percentage of the second benefit agent.

14. The cosmetic device according to claim 1 wherein the first and second benefit agents are selected from the group consisting of anti-wrinkle actives, anti-skin atrophy actives, skin barrier repair aids, and mixtures thereof.

15. The cosmetic device according to claim 1 wherein the first and second benefit agents are niacinamide.

16. The cosmetic devise according to claim 1 wherein the weight ratio of the coating composition to the gel sheet is from about 1:100 to about 2:1.

* * * * *